United States Patent [19]

Delprato et al.

[11] Patent Number: 4,668,610
[45] Date of Patent: May 26, 1987

[54] 2-EQUIVALENT CYAN DYE-FORMING 5-HYDROXY-6-ACYLAMINO-BENZOXAZOLE-2-ONE COUPLERS, SILVER HALIDE PHOTOGRAPHIC ELEMENTS AND PROCESSES EMPLOYING THEM

[75] Inventors: Ivano Delprato, Montenotte; Francesco Squarcia, Bologna, both of Italy

[73] Assignee: Minnesota Mining and Manufacturing Company, St. Paul, Minn.

[21] Appl. No.: 833,954

[22] Filed: Feb. 27, 1986

[30] Foreign Application Priority Data

Mar. 1, 1985 [IT] Italy ................................ 19737 A/85

[51] Int. Cl.$^4$ .......................... G03C 1/40; G03C 7/34
[52] U.S. Cl. .................................... 430/385; 430/553; 430/558
[58] Field of Search ............... 430/553, 558 A, 558 R, 430/552, 385

[56] References Cited

U.S. PATENT DOCUMENTS 4,036,643  7/1977  Viro et al. ........................... 430/553
4,591,548  5/1986  Delprato ............................. 430/558

*Primary Examiner*—Richard L. Schilling
*Attorney, Agent, or Firm*—Donald M. Sell; James A. Smith; Mark A. Litman

[57] ABSTRACT

5-hydroxy-6-acylamino-benzoxazole-2-one compounds, such as those responding to the formula:

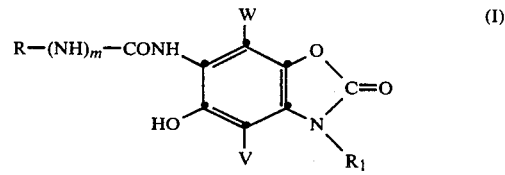

wherein m is 0, 1; R represents a substituted or unsubstituted alkyl, aryl group or a heterocyclic group; $R_1$ represents a substituted or unsubstituted alkyl or aryl group or $R_2$—X—, wherein X represents a member selected from the group consisting of CO, $SO_2$, OCOCO and NHCO and $R_2$ represents a substituted or unsubstituted alkyl group or a substituted or unsubstituted aryl group; and V and W, the same or different, represent hydrogen, halogen or a lower alkyl or alkoxy group, are described as cyan dye-forming couplers for use in silver halide color photographic elements and processes.

10 Claims, No Drawings

2-EQUIVALENT CYAN DYE-FORMING 5-HYDROXY-6-ACYLAMINO-BENZOXAZOLE-2-ONE COUPLERS, SILVER HALIDE PHOTOGRAPHIC ELEMENTS AND PROCESSES EMPLOYING THEM

FIELD OF THE INVENTION

The present invention relates to 2-equivalent cyan dye-forming 5-hydroxy-6-acylamino-benzoxazole-2-one couplers and to silver halide photographic elements and processes employing them.

BACKGROUND OF THE ART

It is known that the development of the light-sensitive silver halides of photographic elements can produce color photographic images. A silver image is produced by means of an aromatic primary amino type developer compound in the presence of color couplers which react with the oxidized developing substance to form a dye in the areas corresponding to the silver image.

In the subtractive three-color photographic process, light sensitive color photographic elements are used which include, coated on a support base, one or more red-sensitive silver halide emulsion layers, one or more green-sensitive silver halide emulsion layers, and one or more blue-sensitive silver halide emulsion layers, wherein upon color development cyan, magenta and yellow dye images are respectively formed.

The couplers normally used to produce cyan image dyes derive from phenols and naphthols (as described in U.S. Pat. Nos. 2,367,351; 2,423,730; 2,474,293; 2,772,161; 2,772,162; 2,895,826; 2,920,961; 3,002,836; 3,476,563; 3,880,661; in French Pat. Nos. 1,478,188 and 1,497,043 and in GB Pat. No. 2,070,000). These types of couplers can be used either in photographic layers or in the baths. In the former case, when it is desired they do not migrate from a layer into another, they can have ballasting substituents and they can bear also hydrophilic or hydrophobic substituents if they must be introduced into photographic layers, respectively, dissolved in water or in an organic solvent. Upon reaction with the oxidation products of the aromatic primary amino type developing agents, such couplers give indoaniline dyes under consumption of four equivalents of silver ions per mole of dye and, preferably, two equivalents of silver ions per mole of dye when the reactive methine group (in the para position to the phenolic hydroxylic group) is substituted with atoms and groups which are splitted off during the coupling reaction.

In the practical use of the cyan dye-forming couplers in the photographic processings, the choice of such couplers is very important because some characteristics of the dyes formed after development, i.e. stability to light, heat and humidity, stability towards the reduction by ferrous ions present in the processing, depend upon the kind of the coupler used.

The loss of density due to an insufficient stability of the dye is a cause of color imbalance in the developed photographic material. Such loss occurs with indoaniline dyes when the bleaching and bleach-fixing baths have an insufficiently high redox potential (for instance when in the bleaching bath, containing ferric ions, there is a too high concentration of ferrous ions).

An aspect of the present invention is therefore to provide a new class of cyan dye-forming 2-equivalent couplers with characteristics suitable to an optimal use in the photographic materials.

SUMMARY OF THE INVENTION

According to the present invention, there are provided 2-equivalent cyan dye-forming 5-hydroxy-6-acylamino-benzoxazole-2-one couplers for use in photography, preferably 2-equivalent cyan dye-forming couplers corresponding to the following general formula:

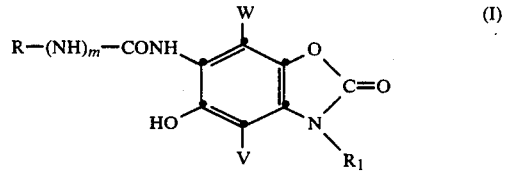

wherein $m = 0, 1$; R represents a substituted or unsubstituted alkyl, aryl or heterocyclic group; $R_1$ represents a substituted or unsubstituted alkyl or aryl group or $R_2$—X— wherein X represents a member selected from the group consisting of —CO—, —SO$_2$—, —OCO-CO— and —NHCO— and $R_2$ represents a substituted or unsubstituted alkyl group or a substituted or unsubstituted aryl group; and V and W, the same or different, represent hydrogen, halogen or a lower alkyl or alkoxy group.

Such couplers, when associated with the silver halide color photographic materials, upon coupling with the oxidized aromatic primary amino type developing agents, open the ether linkage thus forming 2,5-disubstituted cyan indoaniline dyes very stable to light, heat and humidity and to bleaching solutions which have a weak oxidation power or are exhausted.

DETAILED DESCRIPTION OF THE INVENTION

The present invention refers to 2-equivalent 5-hydroxy-6-acylamino-benzoxazole-2-one photographic couplers forming a cyan dye upon reaction with an oxidized aromatic primary amino type developing agent.

The photographic artisan understands that the substituents of each of the compounds represented by the following formulas of the present invention are to be chosen reasonable in size and nature as not to impair their useful characteristics to the purposes of the present invention. The nature and the size of the coupler compounds, as well as of the dyes derived therefrom (upon color development) are near to that of the couplers and dyes which are normally used in the photographic art. For example, in the 6-position of the compounds of the present invention, it is useful to have an acylamino or a ureido group, if it is desired to obtain dyes having, respectively, maximum absorption at shorter or longer wavelengths. In the latter case, such compounds are useful to obtain dyes for color negative photographic materials; in the other case, such obtained dyes are useful in color reversal photographic materials. These acylamino and ureido groups may be substituted with alkyl, aryl, hydroxy, alkoxy, aryloxy, acyloxy, alkylthio, acylamino, sulfonamido, heterocyclic groups, as described in European patent applications Nos. 73,145 and 73,146; or, particularly, with naphthyl or phenyl groups with at least one substituent chosen in the group consisting of trifluoromethyl, nitro, cyano, —COR, —CO₂R, —SO₂R, —SO₂OR, —SO₂, wherein R is an aliphatic or aromatic group, as described in European Pat. No. 87,930 and in German Pat. No. 3,300,412.

Similarly, it is known that the substituents in the 3-position of the compound of the present invention are important to render stable to light, heat and humidity the 2,5-disubstituted cyan indoaniline dyes resulting from the coupling reaction of the couplers of the present invention, when associated with the silver halide color photographic materials, with the oxidized aromatic primary amino type developing agents. The skilled in the art also knows that, if the 2-equivalent cyan dye-forming couplers of the present invention are incorporated into the silver halide emulsion layers, they are, in most instances, required not to diffuse within the layers themselves. A group bearing a ballasting group such as a hydrophobic residue with from 8 to 30 carbon atoms is introduced into the coupler molecule in order to avoid such diffusing process. Such substituent is called "ballasting substituent" and it is linked, directly or through one or more of imino, ether, carbonamido, sulfonamido, ureido, ester, imido, carbamoyy, sulfamoyl, phenylene, etc., groups to the 3-position or 6-position, preferably to the 3-position, of the coupler nucleus. Some examples of ballasting substituents are illustrated in U.S. Pat. No. 4,009,038, in European Pat. Nos. 87,930; 84,100; 87,931; 73,146; 88,563; in German Pat. Nos. 3,300,412; 3,315,012; in Japanese Pat. Nos. J5 8033248; J5 80332500; J5 8031334; J5 8106539. Preferably, such ballasting groups comprise alkyl chains, the total carbon atoms of which are no more than 20.

The substituents in the 4 and 7 positions of these couplers are not very interesting in the photographic art. For this reason, as well as for economical reasons, it is preferred to have in such positions a hydrogen atom, although other groups may replace hydrogen if chosen in size and nature as not to negatively affect the photographic properties of the coupler, as known in the art. Substituents of this type are for example alkyl and alkoxy groups, preferably having 1 to 4 carbon atoms and halogen substituents such as chlorine, bromine and fluorine as ribed, for example, in European patent applications Nos. 113,124; 112,514; in German Pat. Nos. 2,263,171; 2,508,408; 2,529,991; and in Japanese Pat. No. J5 6089740.

Preferably, the present invention relates to the cyan dye-forming couplers described above, wherein the couplers have the general formula:

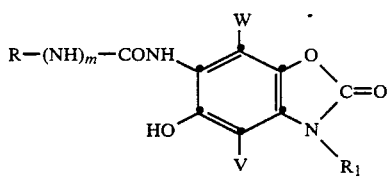
(I)

wherein m is 0, 1; R represents a substituted or unsubstituted alkyl, aryl or heterocyclic group, such as alkyl, perfluoroalkyl, phenyl, naphthyl, alkylphenylene, alkylnaphthylene, thiophene, pyridine, furane, thiazole, benzothiazole, oxazole, imidazole, thiodiazole, preferably having 1 to 20 carbon atoms; $R_1$ represents a substituted or unsubstituted alkyl or aryl group (such as phenyl or naphthyl) or $R_2$—X— wherein X represents a member selected from the group consisting of —CO—, —SO₂—, —OCOCO— and —NHCO— (to form, respectively, RCO—, R₂OCOCO— and R₂NHCO—) and $R_2$ represents a substituted or unsubstituted alkyl group or a substituted or unsubstituted aryl group, both $R_1$ and $R_2$ preferably having 1 to 20 carbon atoms; and V and W, the same or different, represent hydrogen, halogen or a lower alkyl or alkoxy group, preferably having from 1 to 4 carbon atoms.

More preferably, in the general formula (I) above R is an alkylamino or arylamino group (for example methylamino, phenylamino, naphthylamino, etc.), preferably having from 1 to 20 carbon atoms, which may be substituted, $R_1$ is an alkyl group, preferably having from 1 to 20 carbon atoms (for example methyl, ethyl, butyl, hexyl, tridecyl, etc.) and $R_2$ is an alkyl or an aryl group. These groups can be substituted with one or more substituents selected from an alkyl group, a halogen atom, a nitro group, a cyano group, an aryl group (for example phenyl, naphthyl, etc.), an alkoxy group, preferably having from 1 to 20 carbon atoms (for example methoxy, ethoxy, methoxyethoxy, 2-ethylhexyloxy, etc.), an aryloxy group (for example phenoxy, 4-hydroxyphenoxy, 2,4-ditert.-amylphenoxy, naphthoxy, etc.), an acyloxy group (for example acetyloxy, tetradecanoyl, benzoyl, etc.), a sulfamoyl group (for example N-ethylsulfamoyl, N-octadecylsulfamoyl, etc), an acylamino group (for example acetylamino, benzamino, etc.), a diacylamino group (for example succinimido, hydantoinyl, etc.), a ureido group (for example methylureido, phenylureido, etc.), a sulfonamido group (for example methanesulfonamido, dodecanesulfonamido, methoxyethanesulfonamido, etc.), a hydroxy group, a carboxy group, an alkylcarbonyl group (for example acetyl, tetradecanoyl, etc.), an arylcarbonyl group (for example benzoyl, etc.), an alkoxycarbonyl group (for example methoxycarbonyl, benzyloxycarbonyl, etc.), an aryloxycarbonyl bonyl group (for example phenoxycarbonyl, p-tolyloxycarbonyl, etc.), a carbamoyl group (for example N-ethylcarbamoyl, N-ethyl-N-dodecylcarbamoyl, etc.), a heterocyclic group, a mercapto group, an alkylthio group, an arylthio group, an alkylsulfonyl group, an arylsulfonyl group, an acyl group, an aralkyl group.

Most preferably, the present invention relates to the 2-equivalent phenol couplers described above, wherein the coupler has the following formula:

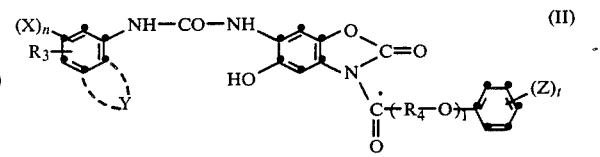
(II)

wherein $R_3$ is selected from the group consisting of —CN, —NO₂, —CF₃, —COOR₅, —COR₅, —SO₂OR₅, —SO₂R₅,

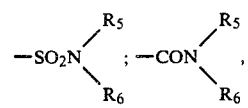

where $R_5$ is an alkyl group (preferably and alkyl group of 1 to 4 carbon atoms) or an aryl group (preferably an unsubstituted or substituted phenyl group whose substituents are preferably chosen within the group consisting of halogen, such as chlorine, bromine and iodine and alkyl and alkoxy groups having 1 to 4 carbon atoms) and $R_6$ is hydrogen, an alkyl group (preferably an alkyl group of 1 to 4 carbon atoms) or an aryl group (preferably an unsusbtituted or substituted phenyl group whose substituents are preferably chosen within the group consisting of halogen, such as chlorine, bromine and iodine and alkyl and alkoxy groups having 1 to 4 carbon atoms), $R_4$ is a divalent straight or branched chain alkylene group having from 1 to 20 carbon atoms; 1 is 0 or 1; Z is an alkyl group of 1 to 20 carbon atoms, particularly an alkyl group of 1 to 8 atoms, such as a secondary or tertiary alkyl group of 4 to 8 carbon atoms, as exemplified by methyl, isopropyl, tert.butyl, tert.-pentyl and pentadecyl; t is 1 to 4; X is a hydrogen or a halogen atom, a hydroxyl, a nitro or a monovalent organic group Y, which is optionally present, completes a 5- or 6-membered condensed ring, n is 1 or 1 to 4 and when n is 2 or more every X may be the same or different.

Still most preferably, the present invention relates to a 2 equivalent phenol coupler as described above, where the coupler has the following formula:

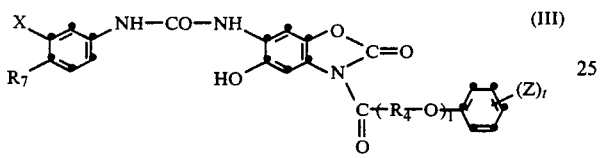

wherein $R_7$ is —CN or —CF$_3$, $R_4$, X and 1 have the same meaning as described above (X preferably being hydrogen or chlorine).

Obviously, with reference to formula (I), the choice of R and $R_1$ substitutents may be very important in order to obtain some coupler and/or dye (derived therefrom upon color development) characteristics. For example, to obtain (upon development) dyes stable even in partially exhausted bleaching baths, R substituent should preferably be an acylamino group.

According to another aspect, the present invention refers to a color silver halide photographic element comprising, coated on a support, at least one light-sensitive silver halide emulsion layer associated with a 2-equivalent cyan dye-forming coupler, as described above and in particular to a color photographic element comprising, coated on a support, at least one light-sensitive silver halide emulsion layer containing a photographic 2-equivalent cyan dye-forming coupler as set forth above, or to a color photographic element comprising, coated on a support, a light-sensitive silver silver halide emulsion layer and in water-permeable relationship therewith a non-light-sensitive colloidal layer containing the 2-equivalent cyan dye-forming coupler as said above.

Such color photographic material comprises at least one blue-sensitive silver emulsion layer, one green-sensitive silver halide emulsion layer and one red-sensitive silver halide emulsion layer, said layers being associated with yellow-dye, magenta-dye and cyan dye-forming couplers, respectively. Preferably, the silver halide emulsion layer comprising the coupler of general formula (I) described above is a red-sensitive silver halide emulsion layer.

The present further relates to a process for forming a cyan-dye image in a photographic element comprising a support and a silver halide emulsion, characterized by the step of developing the exposed element with a silver halide color developing agent in the presence of a 2-equivalent cyan dye-forming 5-hydroxy-6-acylaminobenzoxazole-2-one coupler.

In particular, the present invention relates to a kind of process as described above, in which the silver halide color developing agent developes the exposed element in the presence of a 2-equivalent cyan dye-forming coupler having the general formulas (I) to (III) described above.

In another aspect, the present invention relates to a cyan indoaniline dye obtained, according to the above-described process, upon reaction of the oxidized aromatic primary amino type color developing agent with the 2-equivalent cyan dye-forming couplers above.

Furthermore, the present invention relates also to an exposed and processed photographic element comprising a support and at least one layer containing a cyan-dye image obtained according to the process above.

Examples of couplers included in the scope of the present invention are set forth below in the illustrative preparations.

PREPARATION OF COUPLER (1)

3-[α-(2,4-ditert.-pentylphenoxy)-hexanoyl]-5-hydroxy-6-(4-cyano-phenyl)-ureido-3H-benzoxazole-2-one

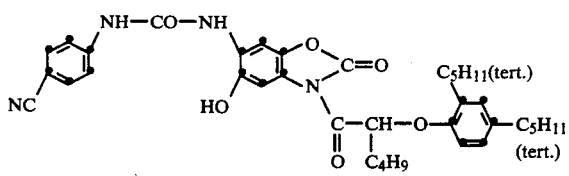

(a) 2-nitro-4-benzyloxyphenol

Fuming nitric acid (d=1.52, 43.6 g, 0.70 mole) was dropwise added under stirring to 4-benzyloxyphenol (138.0 g, 0.69 mole) in ethylacetate (500 ml) at 0° C. The resulting solution was raised at room temperature and then washed in a separatory funnel with sodium hydrogen carbonate in water (saturated solution). The organic layer was separated and evaporated under vacuum and the residual solid was crystallized from methanol (100 ml) to give the nitrophenol (yield of (a): 62.54 g, 36%) as yellow prisms. The product structure was confirmed by NMR and IR spectra.

Percent analysis: Found: C=64.34; H=4.52; N=5.46.

$C_{13}H_{11}NO_4$ requires C=63.67; H=4.52; N=5.71.

(b) 2-amino-4-benzyloxyphenol

Sodium dithionite (174.11 g, 1.0 moles) in water (400 ml) was dropwise added to the nitrophenol ((a), 93.0 g, 0.38 mole) in refluxing ethanol. The resulting solution was refluxed for further 3 hours, then cooled at room temperature and filtered. The obtained solution was concentrated at a final volume of 100 ml. Water (100 ml) was added and the separated amine ((b), 72.0 g, 88%) was recoverd as brown powder.

Percent analysis: Found: C=72.40; H=6.05; N=6.47.

$C_{13}H_{13}NO_2$ requires C=72.54; H=6.90; N=6.51.

(c) 5-benzyloxyloxy-3H-benzoxazole-2-one

Phenylchloroformate (37.7 g, 0.24 mole) in dry acetone (70 ml) was dropwise added under stirring to the aminophenol ((b), 47.0 g, 0.22 mole) in dry acetone (400 ml) and pyridine (53 ml) at room temperature. The solution was refluxed for 2 hours, then cooled at room temperature and evaporated under vacuum. Chloroform (100 ml) and water (400 ml) were added to the residue and the aqueous layer was extracted with chloroform (3×50 ml). The organic layers were collected and evaporated to dryness. Ethyl ether (250 ml) was added to the oily residue and the benzoxazole ((c), 38.7 g, 73.5%) separated as white prisms. The product structure was confirmed by NMR and IR spectra.

Percent analysis: Found: C=69.23; H=4.59; N=5.80.

$C_{14}H_{11}NO_3$ requires C=69.70; H=4.60; N=5.81.

(d) 5-benzyloxy-6-nitro-3H-benzoxazole-2-one

65% nitric acid (d=1.40, 15.3 g, 1.24 mole) was dropwise added under stirring at room temperature to the benzoxazolone ((c), 38.0 g, 1.16 mole) in methylene chloride (500 ml). The resulting solution was stirred for further 2 hours and 100 ml of water was then added thereto. The aqueous layer was extracted with methylene chloride (3×50 ml) and the organic layers were collected and evaporated to dryness under vacuum. The resulting solid was crystallized from toluene (400 ml) to give the nitrobenzoxazolone ((d), 36.9 g, 83%) as yellow prisms. The product structure was confirmed by NMR and IR spectra.

Percent analysis: Found: C=57.71; H=3.38; N=9.78.

$C_{14}H_{10}N_2O_5$ requires C=58.74; H=3.52; N=9.79.

(e) 3-[α-(2,4-ditert.-pentylphenoxy)-hexanoyl]-5-benzyloxy-6-nitro-2H-benzoxazole-2one 60% sodium hydride in oil dispersion (3 g, 0.075 mole) was added to the benzoxazolone ((d), 18.12 g, 0.063 mole) and α-(2,4-ditert.-pentylphenoxy)-hexanoylchloride (23.23 g, 0.063 mole) in dry refluxing toluene (400 ml) and the resulting solution was refluxed for further 2 hours. Water (100 ml) was added and azeotropically distilled. The organic solution was filtered and evaporated to dryness under vacuum. The oily residue was purified by column chromatography on silica gel using toluene as eluant. The obtained yellow oil was crystallized from methanol (150 ml) to give the acylated benzoxazolone ((e), 28.3 g, 72.5%) as white prisms. The product structure was confirmed by NMR and IR spectra.

Percent analysis: Found: C=70.27; H=7.25; N=4.45.

$C_{36}H_{44}N_2O_7$ requres C=70.11; H=7.19; N=4.54.

(f) 3-[α-(2,4-ditert.-pentylphenoxy)-hexanoyl]-5-hydroxy-6-amino-3H-benzoxazole-2-one The nitro compound ((e), 8.0 g, 0.016 mole) in THF (100 ml) was reduced and debenzylated under 25 PSI hydrogen pressure at room temperature in the presence of 10% Pd on charcoal. The resulting amine (f) was not isolated due to easy oxidation by air oxygen.

(g) Coupler 1

4-cyanophenyl-isocyanate (38 g, 0.025 mole) was added to the amine ((f), 12.5 g, 0.025 mole) in TMF (100 ml) and stirred for 30 minutes. The resulting solution was evaporated and the solid residue washed with hot toluene (2×100 ml) to give the coupler ((g), 5.6 g, 35%) as white prisms. The coupler structure was confirmed by NMR and IR spectra.

Percent analysis: Found: C=67.94; H=6.98; N=8.49.

$C_{37}H_{44}N_4O_6$ requires C=69.35; H=6.92; N=8.74.

PREPARATION OF COUPLER (2)

3-[α-(2,4-ditert.-pentylphenoxy)-hexanoyl]-5-hydroxy-6-(4-trifluoro-methylphenyl)-ureido-3H-benzoxazole-2-one

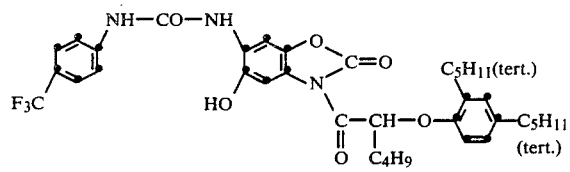

4-trifluoromethylphenyl isocyanate (2.5 g, 0.013 mole) was added to the amine (f) (5.86 g, 0.012 mole) in THF (100 ml) and stirred for 30 minutes. The resulting solution was evaporated to dryness and the grey oily residue was purified by column chromatography on silica gel using ethyl ether-petrol ether 50:50 mixture as eluant to give Coupler (2) (365 g, 44.0%) as white prisms. The product structure was confirmed by NMR and IR spectra.

Percent analysis: Found: C=64.49; H=6.52; N=5.83.

$C_{37}H_{44}F_3N_3O_6$ requires C=64.99; H=6.49; N=6.15.

PREPARATION OF COUPLER (3)

3-[α-(2,4-ditert.-pentylphenoxy)-hexanoyl]-5-hydroxy-6-perfluorobutyroylamino-3H-benzoxazole-2-one

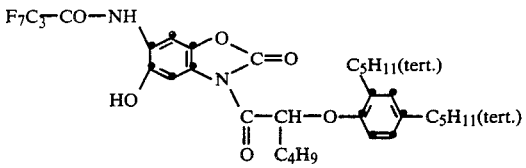

Perfluorobutyroylchloride (7.6 g, 0.032 mole) was added with stirring at room temperature to the amine (f) (18.7 g, 0.03186 mole) in dry THF and pyridine (20 ml). The separated solid was filtered off and the organic solution evaporated to dryness. The residue was crystallized from heptane (50 ml) to give the coupler (6.51 g, 29%) as white prisms. The product structure was confirmed by NMR spectrum.

Percent analysis: Found: C=56.96; H=5.57; N=4.08.

$C_{33}H_{39}N_2O_6F_7$ requires C=57.22; H=5.68; N=4.04.

According to the present invention, color photographic elements present at least one silver halide emulsion layer associated with a 2-equivalent cyan dye-forming coupler of the present invention.

As used herein, the word "associated" means that the 2-equivalent cyan dye-forming couplers of the present invention and the silver halide emulsions are positioned in such a way as to image-wise produce in the photographic layers upon coupling with the oxidized aromatic primary amine type developing agents very stable cyan indoaniline dyes. Such 2-equivalent cyan dye-forming couplers may be incorporated in the silver halide emulsion layer, in an adjacent layer or in the processing solutions.

In a preferred form, the 2-equivalent cyan dye-forming couplers are incorporated in the silver halide emulsion layer. In order to introduce the couplers of the present invention into the silver halide emulsion layer, some conventional methods known to the skilled in the art can be employed. According to U.S. Pat. Nos. 2,322,027; 2,801,170; 2,801,171 and 2,991,177, the couplers can be incorporated into the silver halide emulsion layer by the dispersion technique, which consists of dissolving the coupler in a water-immiscible organic solvent and then dispersing such a solution in a hydrophilic colloidal binder under the form of very small droplets. The preferred colloidal binder is gelatin, even if some other kinds of binders can be used.

Another type of introduction of the couplers into the silver halide emulsion layer consists of the so-called "loaded-latex technique". A detailed description of such technique can be found in BE Pat. Nos. 853,512 and 869,816; in U.S. Pat. Nos. 4,214,047 and 4,199,363 and in EP Pat. No. 141,921. It consists of mixing a solution of the coupler in a water-miscible organic solvent with a polymeric latex consisting of water as a continuous phase and of polymeric particles having a mean diameter ranging from 0.02 to 0.2 micron as a dispersed phase.

Another useful method is further the Fisher process. According to such a process, couplers having a water-soluble group, such as a carboxyl group, a hydroxy group, a sulfonic group or a sulfonamido group, can be added to the photographic layer for example by dissolving them in an alkaline water solution.

The cyan dye-forming couplers of the present invention are generally incorporated into a red-sensitive silver halide emulsion layer to form one of the differently sensitized silver halide emulsion layers of a multilayer color photographic element. Such elements generally comprise a support base having coated thereon one or more red sensitive silver halide emulsion layers, one or more green-sensitive silver halide emulsion layers, one or more blue-sensitive silver halide emulsion layers and additionally filter layers, interlayers, protective layers and sub-layers. The layer units can be coated in any conventional order, but in a preferred layer arrangement, the red-responsive layer unit is coated nearest the support and is overcoated by the green-responsive layer unit, a yellow filter layer and a blue-responsive layer unit.

The layer units are each associated with at least one image dye forming compound. (By "associated" is meant that the silver halide emulsion and the dye forming compounds are so arranged in relation to each other that an interaction between them can take place to produce an image-wise correspondance between the silver image formed and the dye image).

Incorporated dye-forming couplers constitute exemplary preferred image-dye providing compounds. The blue, green and red-responsive layer units preferably contain yellow, magenta and cyan image-dye providing couplers, respectively.

The most useful yellow-color forming couplers are conventional open-chain ketomethylene type couplers. Particular examples of such couplers are benzoylacetanilide type and pivaloyl acetanilide type compounds. A kind of yellow-color forming couplers that can be used is specifically described in U.S. Pat. Nos. 2,875,057; 3,265,506; 3,408,194; 3,551,155; 3,682,322; 3,725,072 and 3,891,445; in West German patent application (OLS) Ser. Nos. 2,219,917; 2,261,361 and 2,414,006; in British Pat. No. 1,425,020; in Japanese patent publication No. 10,783/76; in Japanese patent application (OPI) Ser. Nos. 26/133/72; 73,147/73; 102,636/76; 6,341/75; 123,342/75; 130,442/75; 1,827/76; 87,650/75; 82,424/77 and 115,219/77.

The most useful magenta-color forming couplers are conventional pyrazolone type compounds, indazolone type compounds, cyanoacetyl compounds, etc., and particularly preferred couplers are pyrazolone type compounds. Such kind of magenta-color forming couplers are described for example in U.S. Pat. Nos. 2,600,788; 2,983,608; 3,062,653; 3,127,269; 3,311,476; 3,419,391; 3,519,429; 3,558,319; 3,582,322; 3,615,506; 3,834,908 and 3,891,445; in West German Pat. No. 1,810,464; in West German patent application (OLS) Ser. Nos. 2,408,665; 2,417,945; 2,418,959 and 2,424,467; in Japanese patent application (OPI) Ser. Nos. 20,826/76; 58,922/77; 129,538/74; 74,027/74; 159,336/75; 42,121/77; 74,028/74; 60,233/75; 26,541/76 and 55,122/78.

In addition to the 2-equivalent cyan dye-forming couplers of the present invention, phenol type compounds, naphthol type compounds, etc. can be employed as cyan-color forming couplers. Specific examples of cyan-color forming couplers which can be used are those described for example in U.S. Pat. Nos. 2,369,929; 2,434,272; 2,474,293; 2,521,908; 2,895,826; 3,034,892; 3,311,476; 3,458,315; 3,476,563; 3,583,971; 3,591,383; 3,767,411 and 4,004,929; in West German patent application (OLS) Ser. Nos. 2,414,830 and 2,454,329 and in Japanese patent application (OPI) Ser. Nos. 59,838/73; 26,034/76; 5,055/73; 146,828/76; 69,624/77 and 90,932/77.

Colored couplers which can be used include those described for example in U.S. Pat. Nos. 3,476,560; 2,521,908 and 3,034,892; in Japanese patent publication Nos. 2,016/69; 22,335/63; 11,304/67 and 32,461/69; in Japanese patent application (OPI) Ser. Nos. 26,034/76 and 42,121/77 and in West German patent application (OLS) Ser. No. 2,418,959.

DIR couplers which can be used comprise those described for example in U.S. Pat. Nos. 3,227,554; 3,617,291; 3,701,783; 3,790,384 and 3,632,345; in West German patent application (OLS) Ser. Nos. 2,414,006; 2,454,301 and 2,454,329; in British Pat. No. 953,454; in Japanese patent application (OPI) Ser. Nos. 69,624/77; 122,335/74 and 16,141/76.

In addition to DIR couplers, some other compounds which release development inhibitors upon development can also be present in the light-sensitive material. Such kind of DIR compounds is for example described in U.S. Pat. Nos. 3,297,445 and 3,379,529; in West German patent application (OLS) Ser. No. 2,417,914; in Japanese patent application (OPI) Ser. Nos. 15,271/77 and 9,116/78.

Two or more kinds of the couplers described above can be incorporated in the same layer, or the same coupler can also be present in two or more layers.

Said couplers can be introduced into the silver halide emulsion layers of the photographic materials by using some of the methods described above. Moreover, said couplers are made non-diffusing into the layers by means of the above described ballasting groups.

The present invention is not limited to photographic elements with a particular type of emulsion or silver halide. It can therefore find an application with photographic elements containing different types of emulsion or of silver halides, such as for instance those described in Research Disclosure 17643, I, December 1978.

The emulsion which can be used in the present invention can be chemically and optically sensitized as described in Research Disclosure 17643, III and IV, December 1978. It can contain optical brighteners, antifogging agents and stabilizers, filtering and antihalo dyes, hardeners, coating aids, plasticizers and lubricants and other auxiliary substances as described for instance in Research Disclosure 17643, V, VI, VIII, X, XI and XII, December 1978.

The layers of the photographic emulsion and the layers of the photographic element can contain various colloids, alone or in combination, such as binding materials, as for instance described in Research Disclosure 17643, IX, December 1978.

The photographic elements which can be used in the present invention can contain orthochromatic or panchromatic emulsions, as well as unsensitized emulsions. In particular and more preferably, they can be emulsions for color photography containing color-forming couplers, as described in Research Disclosure 17643, VII, December 1978. Such photographic elements, in particular, can be of the negative color print type or of the reversal type, of the color paper type or of the "movie" positive type. Of course, unconventional photographic materials of the "transfer" type, which make use of negative or direct positive emulsions, such as for instance those described in U.S. Pat. Nos. 3,227,550 and 3,227,551, can use the couplers of the present invention.

The above described emulsions can be coated onto several support bases (cellulose triacetate, paper, resin-coated paper, polyester included) by adopting various methods, as described in Research Disclosure 17643, XV and XVII, December 1978.

For the production of color photographic images according to the present invention, the silver halide emulsion layers exposed to light radiations to form a latent image, are developed with a compound of the primary aromatic amine type in the presence of the color couplers. Suitable developing compounds are in particular the p-phenylene diamine derivatives, for example 2-amino-5-diethylamino-toluene chlorohydrate (called CD2), 4-amino-N-ethyl-N-($\beta$-methansulfonamidoethyl)-m-toluidine sesquisulfate monohydrate (called CD3), 4-amino-3-methyl-N-ethyl-N-($\beta$-hydroxyethyl)-aniline sulfate (called CD4).

After color development, the image-wise developed metallic silver and the remaining silver salts generally must be removed from the photographic material. This is performed in separate bleaching and fixing baths or in a single bath, called blix, which bleaches and fixes the image in a single step. The bleaching bath generally is a water solution having a pH equal to 5.60 and containing an oxidizing agent, normally a complex salt of an alkali metal or of ammonium and of trivalent iron with an organic acid, e.g. EDTA.Fe.NH$_4$, where EDTA is the ethylenediaminotetracetic acid. While processing, this bath is continuously aired to oxidize the divalent iron which forms while bleaching the silver image and regenerated, as known in the art, to maintain the bleach effectiveness. The bad working of these operations causes the drawback of the loss of cyan density in the absence of the couplers of the present invention.

Further to the above mentioned oxidizing agents, the blix bath contains known fixing agents, such as for instance ammonium or alkali metal thiosulfates.

Both bleaching and fixing baths can contain other additives, e.g. polyalkyleneoxide derivatives, as described in GB Pat. No. 933,008 in order to increase the effectiveness of the bath, or oxythioethers known as bleach eccelerators.

The present invention is now explained in deeper details with reference to the examples below, but it should not be construed as being limited thereto.

EXAMPLE 1

A photographic material was prepared by coating a cellulose acetate base with a light-sensitive layer comprising a mixture of two negative emulsions (silver bromo-iodide and silver bromo-chloro-iodide) containing 1.3 g/m$^2$ of silver, 2.76 g/m$^2$ of gelatin and the coupler described above in a quantity of $1.34 \times 10^{-3}$ moles, dissolved in dibutylphthalate-tricresylphosphate in a quantity of 80% by weight.

Another material was obtained in the same way, but using the reference coupler 1-hydroxy-2-[$\delta$-(2',4'-ditert.-amylphenoxy)-n-butyl]-naphthamide of formula:

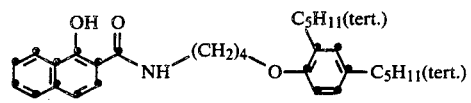

Samples of each material were exposed through a sensitometric wedge and processed in a processing bath having the following composition:

| | |
|---|---|
| K$_2$CO$_3$ | 35.00 g |
| Na$_2$SO$_3$ | 4.25 g |
| KJ | 1.20 mg |
| NaBr | 1.30 g |
| NH$_2$OH.½ H$_2$SO$_4$ | 2.00 g |
| Anticalcium Kodak no. 3 | 2.50 g |
| CD$_4$ | 4.75 g |
| Water up to | 1,000 ml |
| pH | 10.00 |

The following results were obtained:

| | λmax | Dmin | Dmax |
|---|---|---|---|
| Coupler 1 | 686 | 0.22 | 1.50 |
| Coupler 2 | 684 | 0.21 | 1.55 |
| Ref. Coupler | 692 | 0.13 | 1.30 |

The above reported results show that after exposure and development good quality images are obtained by introducing the couplers of the present invention into a silver halide photographic emulsion. The stability to light, heat and humidity of the dyes results good as well. These two compounds proved to be highly reactive when used as two-equivalent cyan couplers in color photographic materials for color development with p-phenylene diamine developers.

EXAMPLE 2

A photographic material similar to that of Example 1 but containing Coupler (3) was exposed and processed as described in Example 1. The following results were obtained.

| λmax | Dmin | Dmax |
| --- | --- | --- |
| 666 | 0.10 | 1.70 |

The coupler turned out to be highly reactive with a low Dmin value.

We claim:

1. A color photographic element comprising coated on a support at least one light-sensitive silver halide emulsion layer associated with a 2-equivalent cyan dye-forming 5-hydroxy-6-acylamino-benzoxazole-2-one coupler.

2. A light-sensitive color photographic element comprising coated on a support at least one light-sensitive gelatin silver halide emulsion layer and containing in the light-sensitive emulsion layer or in a non light-sensitive water-permeable colloidal layer in water-permeable relationship with said light-sensitive silver halide emulsion layer a 2-equivalent cyan dye-forming coupler of the formula:

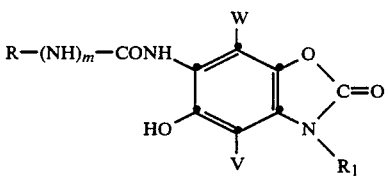

wherein m is 0, 1; R represents a substituted or unsubstituted alkyl group, a substituted or unsubstituted aryl group or a substituted or unsubstituted heterocyclic group; $R_1$ represents a substituted or unsubstituted alkyl or aryl group or $R_2$—X— wherein X represents a member selected from the group consisting of —CO—, —SO$_2$—, —OCOCO— and —NHCO— and $R_2$ represents a substituted or unsubstituted alkyl group or a substituted or unsubstituted aryl group; and V and W, the same or different, represent hydrogen, halogen or a lower alkyl or lower alkoxy group.

3. The color photographic element of claim 2, wherein the silver halide emulsion layer is a red-sensitive emulsion layer.

4. The color photographic element of claim 3, wherein said photographic material further comprises a blue-sensitive silver halide emulsion layer and a green-sensitive silver halide emulsion layer.

5. The color photographic element of claim 3, wherein said blue-sensitive silver halide emulsion layer comprises associated therewith a yellow-dye forming coupler and said green-sensitive silver halide emulsion layer comprises associated therewith a magenta-dye forming coupler.

6. A process for forming a cyan dye image in an exposed photographic element comprising a support and a gelatin silver halide emulsion, characterized by the step of developing the exposed element with a silver halide color developing agent in the presence of a 2-equivalent cyan dye-forming 5-hydroxy-6-acylamino-benzoxazole-2-one coupler, said coupler reacting with oxidized said silver halide developing agent to form a cyan dye.

7. A light-sensitive color photographic element comprising coated on a support at least one light-sensitive gelatin silver halide emulsion layer and containing in the light-sensitive emulsion layer or in a non light-sensitive water-permeable colloidal layer in water-permeable relationship with said light-sensitive silver halide emulsion layer a 2-equivalent cyan dye-forming coupler of the formula:

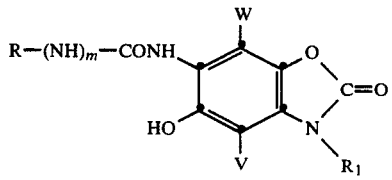

wherein m is 0, 1; $R_1$ represents a substituted or unsubstituted alkyl or $R_2$—X— wherein X represents a member selected from the group consisting of —CO—, —SO$_2$—, —OCOCO— and —NHCO—; and V and W, the same or different, represent hydrogen, halogen or a lower alkyl or lower alkoxy group and characterized in that R is an alkylamino or arylamino group which may be substituted, and $R_2$ is an alkyl group or an aryl group, such groups being unsubstituted or substituted with one or more substituents selected from an alkyl group, a halogen atom, a nitro group, a cyano group, an aryl group, an alkoxy group, an aryloxy group, an acyloxy group, a sulfamoyl group, an acylamino group, a diacylamino group, a ureido group, a sulfonamido group, a hydroxy group, a heterocyclic group, a mercapto group, an alkylthio group, an arylthio group, an alkylsulfonyl group, an arylsulfonyl group, an acyl group, an aralkyl group, an alkylcarbonyl group, an arylcarbonyl group, an alkoxycarbonyl group, an aryloxycarbonyl group, a carboxy group and a carbamoyl group.

8. A light-sensitive color photographic element comprising coated on a support at least one light-sensitive gelatin silver halide emulsion layer and containing in the light-sensitive emulsion layer or in a non light-sensitive water-permeable colloidal layer in water-permeable relationship with said light-sensitive silver halide emulsion layer a 2-equivalent cyan dye-forming coupler of the formula:

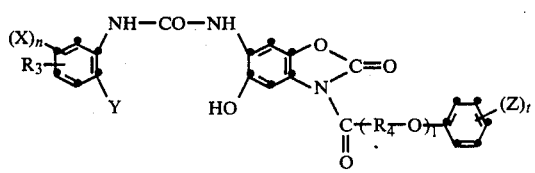

wherein $R_3$ is CN, NO$_2$, CF$_3$, COOR$_5$, COR$_5$, SO$_2$OR$_5$, SO$_2$R$_5$,

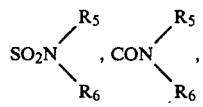

where $R_5$ is an alkyl or an aryl and $R_6$ is hydrogen, an alkyl or aryl group; X is hydrogen, halogen, OH, nitro or a monovalent organic group; n is 1 or 1 to 4 and when n is 2 or more each X may be the same or different; Y, which is optionally present, completes a 5- or 6-membered condensed ring; $R_4$ is a divalent straight or branched alkylene group having from 1 to 20 carbon atoms; l is 0 or 1; Z is an alkyl group having from 1 to 20 carbon atoms; t is 1 to 4.

9. A light-sensitive color photographic element comprising coated on a support at least one light-sensitive gelatin silver halide emulsion layer and containing in the light-sensitive emulsion layer or in a non light-sensitive water-permeable colloidal layer in water-permeable relationship with said light-sensitive silver halide emulsion layer a 2-equivalent cyan dye-forming coupler of the formula:

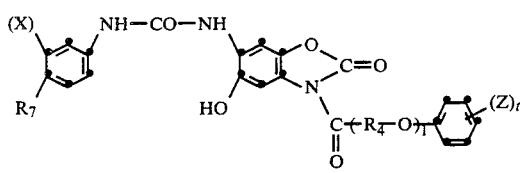

wherein $R_7$ is CN or $CF_3$ and $R_4$ is a divalent straight or branched alkylene group having from 1 to 20 carbon atoms; 1 is 0 or 1; Z is an alkyl group having from 1 to 20 carbon atoms; t is 1 to 4; and X is selected from the group consisting of hydrogen, halogen, OH, nitro, and monovalent organic group.

10. A process for forming a cyan dye image in an exposed photographic element comprising a support and a gelatin silver halide emulsion, characterized by the step of developing the exposed element with a silver halide color developing agent in the presence of a 2-equivalent cyan dye-forming 5-hydroxy-6-acylaminobenzoxazole-2-one coupler of the general formula

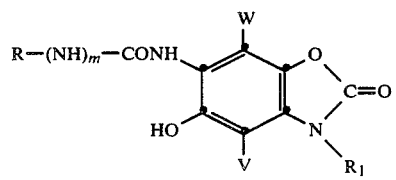

wherein m is 0, 1; R represents a substituted or unsubstituted alkyl group, a substituted or unsubstituted aryl group or a substituted or unsubstituted heterocyclic group; $R_1$ represents a substituted or unsubstituted alkyl or aryl group or $R_2$—X— wherein X represents a member selected from the group consisting of —CO—, —$SO_2$—, —OCOCO— and —NHCO— and $R_2$ represents a substituted or unsubstituted alkyl group or a substituted or unsubstituted aryl group; and V and W, the same or different, represent hydrogen, halogen or a lower alkyl or alkoxy group and said coupler reacting with oxidized said silver halide color developing agent to form a cyan dye.

* * * * *